United States Patent
Maurya et al.

(10) Patent No.: US 6,617,313 B1
(45) Date of Patent: Sep. 9, 2003

(54) **GLUCOPYRANOSIDE AND PROCESS OF ISOLATION THEREOF FROM *PTEROCARPUS MARSUPIUM* PHARMACEUTICAL COMPOSITION CONTAINING THE SAME AND USE THEREOF**

(75) Inventors: Rakesh Maurya, Jammu (IN); Sukhdev Swami Handa, Jammu (IN); Rajinder Singh, Jammu (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/099,293

(22) Filed: Mar. 13, 2002

(51) Int. Cl.$^7$ .................... A61K 31/70; A61K 31/7042; A61K 31/7048
(52) U.S. Cl. .................... 514/23; 514/866; 536/1.1; 536/124; 536/127; 536/128
(58) Field of Search .................... 514/23, 866, 183; 536/1.1, 124, 127, 128

(56) References Cited

U.S. PATENT DOCUMENTS 5,886,029 A  3/1999  Dhaliwal .................... 514/456

FOREIGN PATENT DOCUMENTS

EP  0 956 867 A1  11/1999

OTHER PUBLICATIONS

Dama Adinarayana et al., *Phytochemistry*, 1982, 21(5):1083–1085.
Dama Adinarayana, *Zeitschrift Fur Naturforschung*, 1982, 37C:145–147.
K.R. Kirtikar et al., *Indian Medicinal Plants*, 1975, 3:2126–2137.
R.N. Chopra et al., *Indigenous Drugs of India*, 1958, p. 522.
S.K. Jain, *Medicinal Plants*, 1968, 116–118.
J. Mitra et al., *Phytochemistry*, 1983, 22(10):2326–2327.
J. Matthew et al., *Current Science*, 1984, 53(11):576–577.
J. Matthew et al., *Phytochemistry*, 1983, 22(3):794–795.
A.V. Subba Rao et al., *Phytochemistry*, 1982, 21(7):1837–1838.
J. Mitra et al., *Phytochemistry*, 1982, 21(9):2429–2430.
Poonam Mohan et al., *Phytochemistry*, 1989, 28(4):1287–1288.
A.V. Subba Rao et al., *Phytochemistry*, 1984, 23(4):897–898.
Subhash C. Jain et al., *Phytochemistry*, 1987, 44(4):765–766.
H. Kolb et al., *Lancet*, 1982, 1303–1304.
E.W. Sheehan et al., *J. Natural Prod.*, 1983, 46(1):232–234.
Padmini Kedar et al., *Maharashtra Medical Journal*, 1981, 28(6):165–169.
R. Maurya et al., *J. Natural Prod.*, 1984, 47(1):179–181.
B.K. Chakravarthy et al., *Lancet*, 1982, 272–273.
S.S Gupta, *Ind. J. Med. Res.*, 1963, 51(4):716–724.
D.S. Shah, *Ind. J. Med. Res.*, 1967, 55(2):166–168.
Barend C.B. Bezuidenhoudt et al., *Phytochemistry*, 1987, 26(2):531–535.
B.K. Chakravarthy et al., *Planta Medica*, 1985, 1, 56–59.
R. Maurya et al, *Heterocycles*, 1982, 19(11):2103–2107.
Prithwi Nath Bhargava, *Proceedings of the Indian Academy of Sciences*, 1947, 24:496–500.
S. Kumar et al., *Ind. J. Physio. and Pharma.*, 1971, 15(2):51.
G.C. Sepaha et al., *J. Ind. Med. Assoc.*, 1956, 27(10):388–391.
PCT Search Report.
Nilima Banerji et al., *J. Inst. Chemists (India)*, 1994, 66, 95–96.
Anjali Ghosh et al., *J. Inst. Chemists (India)*, 1995, 67, 50–54.
M. Manickam et al., *J. Nat. Prod.*, 1997, 60, 609–610.

*Primary Examiner*—Samuel Barts
*Assistant Examiner*—Michael C. Henry
(74) *Attorney, Agent, or Firm*—Morgan & Finnegan, LLP

(57) ABSTRACT

A novel glucopyranoside, 2,6-dihydroxy-2-(P-hydroxybenzyl)-3(2H) benzofuran-7-C-β-D-glucopyranoside of the formula 1

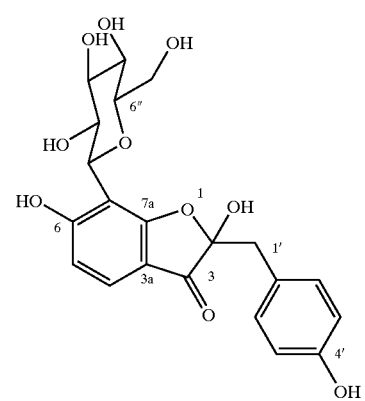

isolated from *Pterocarpus marsupium* and to a process for the isolation thereof is disclosed. The invention also relates to a pharmaceutical composition containing 2,6-dihydroxy-2-(P-hydroxybenzyl)-3(2H)benzofuran-7-C-β-D-glucopyranoside and to method for the treatment of diabetes using said compound.

10 Claims, No Drawings

GLUCOPYRANOSIDE AND PROCESS OF ISOLATION THEREOF FROM *PTEROCARPUS MARSUPIUM* PHARMACEUTICAL COMPOSITION CONTAINING THE SAME AND USE THEREOF

FIELD OF THE INVENTION

The present invention relates to a novel glucopyranoside, 2,6-dihydroxy-2-(P-hydroxybenzyl)-3(2H)benzofuran-7-C-β-D-glucopyranoside of the formula 1

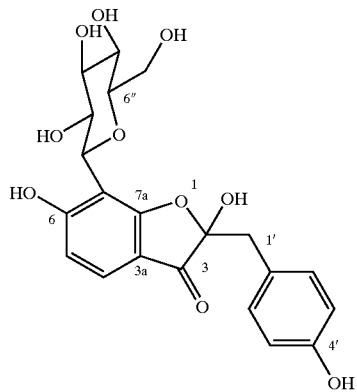

The present invention also relates to a process for the isolation of said novel glucopyranoside of formula 1 from *Pterocarpus marsupium*.

More particularly, the present invention relates to a process of isolation of 2,6-dihydroxy-2-(P-hydroxybenzyl)-3 (2H)benzofuran-7-C-β-D-glucopyranoside of formula 1, from *Pterocarpus marsupium*. The present invention also relates to a pharmaceutical composition containing 2,6-dihydroxy-2-(P-hydroxybenzyl)-3(2H) benzofuran-7-C-β-D-glucopyranoside of the formula 1 and to method for the treatment of diabetes using said compound of formula 1.

BACKGROUND OF THE INVENTION

*Pterocarpus marsupium* Roxb (Leguminosae) also known as Indian Kino tree or Bijasar, is common in the hilly regions of central and peninsular India [Jain, S. K., Medicinal Plants, National Book Trust, New Delhi, 1968, p. 116]. The extracts of leaves, flowers and gum of this tree have been used medicinally in the treatment of diarrhea, toothache, fever, urinary tract and skin infections. [Chopra, R. N., Chopra, I. C., Handa, K. L. and Kapur, L. D., Indigenous Drugs of India, 2nd Ed., Dhar, U. N. and Sons Private Limited, Calcutta, 1958, p. 522]. The extract of the bark has long been regarded as useful in the therapy of diabetes [Kirtikar, K. R. and Basu, B. D., Indian Medicinal Plants, 2nd Ed., edited by Blatter, E., Cailes, J. F. and Mhaskar, K. S., Singh and Singh, Delhi, India, 1975, p. 2135]. It is reported by Chakravarthy et al [Chakravarthy, B. K., Gupta, S. and Gode, K. D., *Lancet*, 1982, 272 (and references cited therein)] that the active hypoglycemic principle of the bark is (−)-epicatechin and that its effect is due to the regeneration of pancreatic beta cells. However, this claim has been questioned by Kolb et al [Kolb, H., Kiesel, U., Grenlich, B. and Bosch, J. V. D., *Lancet*, 1982, 1303.] and Sheehan et al [Sheehan, E. W., Zemaitis, M. A., Slatkin, D. J. and Schiff, Jr., P. L., Journal of Natural Products, 1983, 46, 232]. It is now felt that further investigation is necessary before (−)-epicatechin can be considered a viable antidiabetic agent for use in human clinical studies.

Practitioners of the Indian System of Medicine are of the view that the heartwood rather than the bark of *Pterocarpus marsupium* is useful for treatment of diabetic patients and that older the plant more efficacious is its heartwood. It is also claimed that only heartwood that is distinctly red in colour and which imparts a red colouration with bluish green fluorescence to water in which it is kept soaked is suitable for use as an antidiabetic drug.

Hypoglycaemic effects of aqueous or alcoholic extracts of heartwood of *Pterocarpus marsupium* have been verified by experimental [Shah, D. S., *Indian Journal of Medical Research*, 1967, 55, 166 and references cited therein; Gupta, S. S., *Indian Journal of Medical Research*, 1963, 51, 716] and clinical studies [Sepha, G. C. and Bose, S. N., *J. Ind. Med. Assoc.*, 1956, 27, 383; Kedar, P. and Chakrabarti, C. H., *Maharashtra Med. J.*, 1981, 28, 165].

The heartwood of *Pterocarpus marsupium* is rich in phenolics. Chemical investigation on heartwood of *P. marsupium* dates back to 1946 but early works [Bhargava, P. N., *Proc. Ind. Acad. Sci.*, 1946, 24A, 496] on this drug are fragmentary in nature. Previous reported studies on this plant disclose the following chemical constituents.

1. The ether extract of *P. marsupium* heartwood furnished isoflavonoid glycol 4,4'-dihydroxy-α-methylhydrobenzoin designated Marsupol [Rao, A. V. S., Mathew, J., *Phytochemistry*, 1982, 21, 1837], a benzofurannone derivative, 2,4'6-trihydroxy-4-methoxybenzo(b) furan-3(2H)-one designated carpusin [Mathew, J. and Rao, A. V. S., *Phytochemistry*, 1983, 22, 794], 2-propanol derivative, 1,3-bis(4-hydroxyphenyl)propan-2-ol, designated propterol [Rao, A. V. S., Mathew, J. and Shankaran, A. V. B., *Phytochemistry*, 1984, 23, 897], 1-(2,4-dihydroxyphenyl)-3-(4-hydroxyphenyl)propan-2-ol designated propterol B [Mathew, J., Rao, A. V. S. and Rambhav, S. *Current Science*, 1984, 53, 576], 6-hydroxy-7-O-methyl-3-(3-hydroxy-4-O-methyl benzyl)chroman-4-one [Jain, S. C., Sharma, S. K., Kumar, R., Rjwansh, V. K. and Babu, V. R., *Phytochemistry*, 1997, 44, 765].

2. Ethyl acetate soluble fraction of alcoholic extract of the heartwood furnished pterosupin β, 2',4,4'-tetrahydroxy-3' (c-β-D-glucopyranoside)dihydrochalcone [Adinarayana, D., Syamsundar, K. V., Seligmann, O., and wagner, H., (Z. Naturforsch., 1982, 37C, 145)], Marsupinol [Trivedi J. J., Indian *J Phys. Pharmacol*, 1997, 15, 51], 5,4'-dimethoxy-8-methylisoflavone-7-O-β-L-rhamnopyranoside, retusin-O-β-D glucopyranoside and irisolidine-7-O-α-L-rhamnopyranoside [Mitra, J. and Joshi, T., *Phytochemistry*, 1982, 21, 2429] and 5,7'-dihydroxy-6-methoxy-7-O-α-L-rhamnopyranoside [Mitra, J. and Joshi, T., *Phytochemistry*, 1983, 22, 2326] obtained from the ethyl acetate soluble fraction of alcoholic extract of the heartwood.

3. Novel benzofuranone derivative, 2,6-dihydroxy-2-(p-hydroxybenzyl)-4-methoxy-3(2H)-benzofuranone designated as marsupin [Maurya, R., Ray, A. B., Duah, F. K., Slatkin, D. J. and Schiff, P. L. Jr., *Heterocycles*, 1982, 19, 2103] along with pterostilbin, (2S)-hydroxyflavone, isoliquiritigenin, liquiritigenin, 7,4'-dihydroxyflavone, 5-deoxykaempferol and 3,7,4'-trihydroxyflavone [Maurya, R., Ray, A. B. Duah, F. K., Slatkin, D. J. and Schiff, P. L. Jr., *J. Nat. Prod.* 1984, 47, 179], two C-glycosides, 8-C-β-D-glucopyranosyl-3,7,4'-trihydroxy and 3,7,3',4'-tetrahydroxy flavone and 3'-C-β-D-glucopyranosyl-α-hydroxy dihydrochalcone [Bezuidenhoudt, B. C. B., Brandt, E. V., and Ferreira, E. V., *Phytochemistry*, 1987, 26, 531] from ethyl acetate extract of defatted heartwood.

4. The petrol extract of *P marsupium* root afforded selin-4 (15)-ene-1β, 11-diol, β-eudesmol, erythrodiol-3- monoacetate and pterostilbene [Adinarayana, D., and Syamasundar, K. V., *Phytochemistry,* 1982, 22, 1083]. Ethanolic extract of *P. marsupium* flowers furnished 4,6,4'-trihydroxyaurone 6-O-rhamnopyranoside and 4,6,4'-trihydroxy-7-methylaurone 4-O-rhamnopyranoside [Mohan, P., and Joshi, T., *Phytochemistry,* 1989, 28, 1287] and ethanolic extract of *P. marsupium* bark furnished (−)-epicatechin [Chakravarthy, B. K., and Gode, K. D., *Planta Medica,* 1985, 56].

However, the prior art does not provide any details about the biological activities associated with such chemical constituents. Also prior art discloses only preparation of ether extract, ethyl acetate extract and ethyl acetate soluble fraction of the alcoholic extract but does not disclose any method of preparing water extracts of heartwood of *Pterocarpus marsupium* and attempting to isolate any chemical constituents therefrom.

OBJECTS OF THE INVENTION

The main object of the invention is to accordingly prepare water extracts of the heartwood of *Pterocarpus marsupium* and to obtain chemical constituents therefrom.

It is another object of the invention to investigate the water extracts of heartwood of *Pterocarpus marsupium* in order to obtain novel bioactive fractions therefrom which could be useful in the treatment of diabetes.

SUMMARY OF THE INVENTION

The above and other objects of the invention are achieved by preparing a n-butanol soluble water extract of investigate the water extract of heartwood of *Pterocarpus marsupium* and isolating a novel bioactive fraction therefrom. 2,6-dihydroxy-2-(P-hydroxybenzyl)-3(2H)benzofuran-7-C-β-D-glucopyranoside was isolated from the n-butanol soluble fraction of the water decoction of the heartwood of *P. marsupium* which has shown antidiabetic activity in both humans and animals. There is no disclosure in the prior art of this compound since work had been done in the art on the ether extract, ethyl acetate extract and ethyl acetate soluble fraction of the alcoholic extract.

Accordingly, the present invention provides a novel glucopyranoside 2,6-dihydroxy-2-(P-hydroxybenzyl)-3(2H) benzofuran-7-C-β-D-glucopyranoside of the formula 1

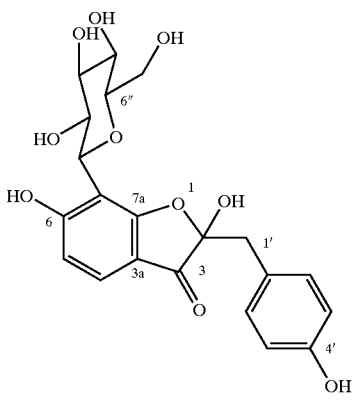

The present invention also provides a process for the isolation of 2,6-dihydroxy-2-(P-hydroxybenzyl)-3(2H) benzofuran-7-C-β-D-glucopyranoside of the formula 1 which comprises:

(a) powdering the heartwood of the plant *Pterocarpus marsupium,*

(b) extracting the powdered plant material with a protic solvent, (c) concentrating the extract to minimum volume and partitioning with different organic solvents of increasing polarity to remove non-polar components, extracting the aqueous layer with polar solvent, removing the solvent to get the residue, (d) isolating the 2,6-dihydroxy -2-(P-hydroxybenzyl)-3 (2H)benzofuran-7-C-β-D-glucopyranoside from the residue.

In one embodiment of the invention, the protic solvent used for preparing the extract in step (b) is selected from the group consisting of water, methanol, ethanol, propanol, butanol and any mixture thereof.

In another embodiment of the invention, the organic solvent used in step (c) to remove the non-polar components is selected from the group consisting of hexane, pet ether and chloroform.

In a further embodiment of the invention the polar solvent used to extract the aqueous layer is selected from ethyl acetate, propanol and butanol.

In another embodiment of the invention, the chromatographic methods used for the isolation of 2,6-dihydroxy-2-(P-hydroxybenzyl)-3(2H)benzofuran-7-C-β-D-glucopyranoside is selected from MPLC, HPLC and flash chromatography.

The present invention also relates to a pharmaceutical composition containing a pharmaceutically effective amount of 2,6-dihydroxy-2-(P-hydroxybenzyl)-3(2H)benzofuran-7-C-β-D-glucopyranoside of formula 1 in a pharmaceutically acceptable carrier.

In one embodiment of the invention, the amount of 2,6-dihydroxy-2-(P-hydroxybenzyl)-3(2H)benzofuran-7-C-β-D-glucopyranoside in said composition is in the range of 0.5 mg to 10 mg per kg of body weight of the patient.

The invention also relates to a method for the treatment of diabetes comprising administering a pharmaceutically effective amount of 2,6-dihydroxy-2-(P-hydroxybenzyl)-3(2H) benzofuran-7-C-β-D-glucopyranoside to a patient.

In one embodiment of the invention, the amount of 2,6-dihydroxy-2-(P-hydroxybenzyl)-3(2H)benzofuran-7-C-β-D-glucopyranoside in said composition is in the range of 0.5 mg to 10 mg per kg of body weight of the patient.

The present invention also relates to the use of 2,6-dihydroxy-2-(P-hydroxybenzyl)-3(2H)benzofuran-7-C-β-D-glucopyranoside in the preparation of a pharmaceutical composition for the treatment of diabetes.

DETAILED DESCRIPTION OF THE INVENTION

The present invention provides a process for the isolation of 2,6-dihydroxy-2-(P-hydroxybenzyl)-3(2H)benzofuran-7-C-β-D-glucopyranoside which comprises:

(a) powdering the heartwood of the plant *Pterocarpus marsupium,*

(b) extracting the powdered plant material so prepared with a protic solvent, (c) concentrating the aqueous extract to minimum volume and partitioning with organic solvents of increasing polarity to remove non-polar components, extracting the aqueous layer with polar solvent, removing the solvent to get the residue;

(d) isolating the 2,6-dihydroxy-2-(P-hydroxybenzyl)-3 (2H)benzofuran-7-C-β-D-glucopyranoside from residue.

The solvent used for preparing the extract may be water, methanol, ethanol, propanol and butanol and like or their mixtures. The organic solvent used in step (c) to remove the non-polar components is selected from the group consisting of hexane, pet ether and chloroform. The polar solvent used to extract the aqueous layer is selected from ethyl acetate, propanol and butanol. The chromatographic methods used for the isolation of 2,6-dihydroxy-2-(P-hydroxybenzyl)-3 (2H)benzofuran-7-C-β-D-glucopyranoside may be MPLC, flash chromatography etc.

In the MPLC method the required eluting solvent is pumped through the column and in the flash chromatography solvent is pushed with air pressure. The compound was assigned the molecular formula $C_{21}H_{22}O_{10}$ on the basis of strong peak at m/z 435 $[M+1]^+$ in the FAB mass spectrum, together with the support of spectroscopic methods.

The compound 2,6-dihydroxy-2-(P-hydroxybenzyl)-3 (2H)benzofuran-7-C-β-D-glucopyranoside was isolated from the n-butanol soluble fraction of the water decoction of the heartwood of P. marsupium which has shown antidiabetic activity in both humans and animals. There is no disclosure in the prior art of this compound since work had been done in the art on the ether extract, ethyl acetate extract and ethyl acetate soluble fraction of the alcoholic extract.

The process of isolating active principle from Pterocarpus marsupium comprises partition of the aqueous extract of powdered heartwood with different organic solvents containing 1–6 carbon atoms in the molecule. 2,6-dihydroxy-2-(P-hydroxybenzyl)-3(2H)benzofuran-7-C-β-D-glucopyranoside of formula 1 is isolated from polar fraction by applying modern chromatographic techniques such as medium pressure liquid chromatography (MPLC), high pressure liquid chromatography (HPLC) and flash chromatography using silica gel (230–400 mesh) and shows hypoglycaemic activity.

The 2,6-dihydroxy-2-(P-hydroxybenzyl)-3(2H) benzofuran-7-C-β-D-glucopyranoside isolated from Pterocarpus marsupium possesses anti-diabetic activity.

The chromatographic methods used for the isolation of 2,6-dihydroxy-2-(p-hydroxybenzyl)-3(2H)benzofuran-7-C-β-D-glucopyranoside may be MPLC, flash chromatography etc. In the MPLC method the solvent is pumped through the column and in the flash chromatography is pushed with air pressure. The compound displayed diagnostic IR absorption at $v_{max}^{KBr}$ 3300, 1680, 1608, 1510, 1444 $cm^{-1}$ for hydroxyls, carbonyl group and aromatic ring. UV spectrum showed absorption maxima $\lambda_{max}^{MeOH}$ 211, 240, 282, 333 nm which underwent bathochromic shift 211, 261, 283, 344 nm in presence of NaOAc.

The $^1H$ NMR spectrum indicated the presence of one benzylic methylene group at δ2.90 (1H, d, J=13.7 Hz) and 3.11 (1H, d, J=13.7 Hz), two ortho-coupled aromatic protons at δ6.61 (1H, d, J=8.5 Hz) and 7.03 (1H, d, J=8.5 Hz) and one $A_2B_2$ aromatic system at δ6.61 (2H, d, J=8.5 Hz) and 7.13 (2H, d, J=8.5 Hz). Further $^1H$ and $^{13}C$ NMR spectra showed signals attributed to one glucose moiety. The C—C coupling was exemplified by $^1H$ and $^{13}C$ heteronuclear correlation of the anomeric proton at δ4.68 (1H, d, J=9.9 Hz) with a carbon doublet at δ79.7 in the region characteristic of $C_1$-substituted glucosides. The coupling constant (J=9.9 Hz) of the signal resulting from the anomeric proton of the glucopyranoside indicated that the glucosidic linkage has β-configuration. A consideration of the spectral data showed $[M+1]^+$ at m/z 435 for $C_{21}H_{22}O_{10}$ with other significant fragment ions at m/z 457 $[M+Na]^+$, 418, 327, 299, 107, 93, further supporting the hypothesis. On the basis, structure of the compound as 2,6-dihydroxy-2-(p-hydroxybenzyl)-3(2H) benzofuran-7-C-β-D-glucopyranoside of the formula 1 was established.

The invention is described in detail by the examples given below which should not be construed to the limit of scope of the present invention.

EXAMPLE 1

The powdered heartwood of Pterocarpus marsupium (1 kg) was percolated with 80% aqueous ethanol (3×3 lits.) for a period of 48 hours. The resultant concentrate was partitioned with hexane, chloroform, propanol and butanol in that order. The polar extract was subjected to MPLC using silica gel (100–200 mesh) for gross fractions with hexane, chloroform, methanol, ethanol in that order. The active compound was purified by repeated MPLC and flash chromatography over silca gel (230–400 mesh) using $CHCl_3$-MeOH (9:1) as solvent, to furnish 2,6-dihydroxy 2-(p-hydroxybenzyl)-3(2H)benzofuran-7-C-δ-D-glucopyranoside of the formula 1, (yield 0.078%), mp. 156–158° C., $[\alpha]_D^{19}$+8.44° (MeOH, c, 0.225).

EXAMPLE 2

The heartwood of Pterocarpus marsupium was extracted with hot water for a period of 4 hours. The resultant concentrate was partitioned between hexane, chloroform, propanol and butanol in that order. The n-butanol polar extract so obtained was subjected to flash chromatography employing silica gel (100–200 mesh) using hexane, chloroform, ethylacetate and methanol as solvent system to afford 2,6-dihydroxy-2-(p-hydroxybenzyl)-3(2H) benzofuran-7-C-β-D-glucopyranoside rich fraction, which on repeated chromatography over silica gel (230–400 mesh) using EtOAc-MeOH (19:1) as solvent, furnished 2,6-dihydroxy-2-(p-hydroxybenzyl)-3(2H)benzofuran-7-C-β-D-glucopyranoside of the formula 1, (yield 0.087%), mp. 157–158° C., $[\alpha]_D^{19}$+8.44° (MeOH, c, 0.225).

EXAMPLE 3

The heartwood of Pterocarpus marsupium was boiled with water (16 times) till 1/4 volume of water is left, filtered, concentrated and partitioned between hexane, chloroform, ethyl acetate, propanol and n-butanol in that order. The polar extract obtained was subjected to column chromatography employing silica gel (60–120 mesh) using hexane, chloroform, ethyl acetate and methanol as solvent system to afford 2,6-dihydroxy-2-(p-hydroxybenzyl)-3(2H) benzofuran-7-C-β-D-glucopyranoside rich fraction. The 2,6-dihydroxy-2-(p-hydroxybenzyl)-3(2H)benzofuran-7-C-β-D-glucopyranoside rich fraction on repeated column chromatography over silica gel (100–200 mesh) using mixture of ethyl acetate-acetone (7:3), furnished 2,6-dihydroxy-2-(p-hydroxybenzyl)-3(2H) benzofuran -7-C-β-D-glucopyranoside of the formula 1 (yield 0.090%), mp. 157–158 ° C., $[\alpha]_D^{19}$+8.44° (MeOH, c, 0.225).

ADVANTAGES

1. The compound obtained 2,6-dihydroxy-2-(p-hydroxybenzyl)-3(2H)benzofuran-7-C-β-D-glucopyranoside is a novel molecule with antidiabetic activity.
2. The method of isolation of 2,6-dihydroxy-2-(p-hydroxybenzyl)-3(2H)benzofuran-7-C-β-D-glucopyranoside is comparatively simple.

We claim:

1. A novel glucopyranoside 2,6-dihydroxy-2-(P-hydroxybenzyl)-3(2H)benzofuran-7-C-β-D-glucopyranoside of the formula 1

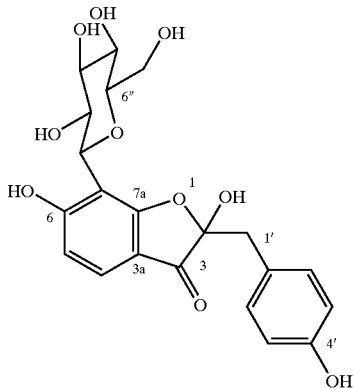

2. Process for the isolation of 2,6-dihydroxy-2-(P-hydroxybenzyl)-3(2H)benzofuran-7-C-β-D-glucopyranoside of the formula 1

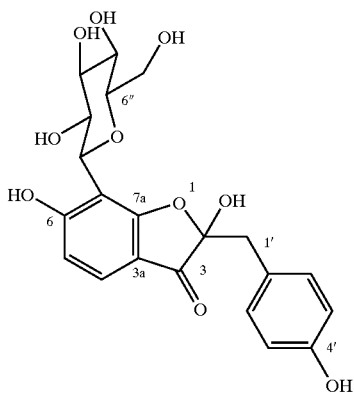

which comprises:

(a) powdering the heartwood of the plant *Pterocarpus marsupium*, (b) extracting the powdered plant material with a protic solvent, (c) concentrating the extract to minimum volume and partitioning with different organic solvents of increasing polarity to remove non-polar components, extracting the aqueous layer with polar solvent, removing the solvent to get the residue, (d) isolating the 2,6-dihydroxy-2-(P-hydroxybenzyl)-3(2H)benzofuran-7-C-β-D-glucopyranoside from the residue.

3. Process as claimed in claim 2 wherein the protic solvent used for preparing the extract in step (b) is selected from the group consisting of water, methanol, ethanol, propanol, butanol and any mixture thereof.

4. Process as claimed in claim 2 wherein the organic solvent used in step (c) to remove the non-polar components is selected from the group consisting of hexane, pet ether and chloroform.

5. Process as claimed in claim 2 wherein the polar solvent used to extract the aqueous layer is selected from ethyl acetate, propanol and butanol.

6. Process as claimed in claim 2 wherein the chromatographic methods used for the isolation of 2,6-dihydroxy-2-(P-hydroxybenzyl)-3(2H)benzofuran-7-C-β-D-glucopyranoside is selected from MPLC, HPLC and flash chromatography.

7. Pharmaceutical composition containing a pharmaceutically effective amount of 2,6-dihydroxy-2-(P-hydroxybenzyl)-3(2H)benzofuran-7-C-β-D-glucopyranoside of formula 1 in a pharmaceutically acceptable carrier.

8. Composition as claimed in claim 7 wherein the amount of 2,6-dihydroxy-2-(P-hydroxybenzyl)-3(2H)benzofuran-7-C-β-D-glucopyranoside in said composition is in the range of 0.5 mg to 10 mg per kg of body weight of the patient.

9. Method for the treatment of diabetes comprising administering a pharmaceutically effective amount of 2,6-dihydroxy-2-(P-hydroxybenzyl)-3(2H)benzofuran-7-C-β-D-glucopyranoside to a patient.

10. Method as claimed in claim 9 wherein the amount of 2,6-dihydroxy-2-(P-hydroxybenzyl)-3(2H)benzofuran-7-C-β-D-glucopyranoside in said composition is in the range of 0.5 mg to 10 mg per kg of body weight of the patient.

* * * * *